United States Patent [19]

Therriault et al.

[11] Patent Number: 4,904,247
[45] Date of Patent: Feb. 27, 1990

[54] PRESSURE-SENSITIVE HYDROPHILIC LAMINATE STRUCTURES FOR USE IN WOUND DRESSING, TRANSDERMAL AND TOPICAL DRUG DELIVERY

[75] Inventors: Donald J. Therriault, Lowell; Samuel C. Temin, Needham, both of Mass.; Kishore R. Shah, Bridgewater, N.J.

[73] Assignee: Kendall Company, Lexington, Mass.

[21] Appl. No.: 782,848

[22] Filed: Oct. 2, 1985

Related U.S. Application Data

[63] Continuation-in-part of Ser. No. 646,550, Aug. 31, 1984, abandoned.

[51] Int. Cl.⁴ .............................................. A61F 13/00
[52] U.S. Cl. .................................... 604/304; 128/156
[58] Field of Search ................ 128/155, 156; 604/304, 604/307, 308

[56] References Cited

U.S. PATENT DOCUMENTS

| | | | |
|---|---|---|---|
| 4,300,820 | 11/1981 | Shah | 525/205 X |
| 4,321,117 | 3/1982 | Kaetsu et al. | 128/156 X |
| 4,323,557 | 4/1982 | Rosso et al. | 128/156 X |
| 4,369,229 | 1/1983 | Shah | 428/508 X |
| 4,462,665 | 7/1984 | Shah | 428/212 X |

Primary Examiner—William R. Dixon, Jr.
Assistant Examiner—Chris Gallo
Attorney, Agent, or Firm—Alvin Isaacs

[57] ABSTRACT

The present invention describes a pressure-sensitive hydrophilic laminate composite comprising contiguous layers of a tacky pressure sensitive hydrophilic polymer blend, and a non-tacky hydrophilic polymer blend. Numerous variations in individual layer formulations allow for a multitude of hydrophilic blend laminate composite structures, which are readily utilizable as wound dressings, and/or transdermal and topical delivery systems incorporating a wide range of bioactive agents. The hydrophilic laminate composite structurese are characterized by ease of application, adhesiveness to skin, high tensile strength, mechanical integrity, transparency, fluid absorbency, and highly effective bacterial barrier properties, and permeability to water vapor, oxygen and drugs and/or bioactive agents. In the preferred embodiments, they are further characterized in their ability to inhibit severe maceration of the wound as well as underlying tissue destruction upon removal.

10 Claims, No Drawings

PRESSURE-SENSITIVE HYDROPHILIC LAMINATE STRUCTURES FOR USE IN WOUND DRESSING, TRANSDERMAL AND TOPICAL DRUG DELIVERY

RELATED APPLICATION

This application is a continuation-in-part of our earlier application, Ser. No. 646,550 filed Aug. 31, 1984 and now abandoned.

BACKGROUND OF THE INVENTION

The present invention relates to wound dressing materials.

The present invention further relates to transdermal and topical drug delivery device constructions.

The present invention more particularly relates to transparent and absorbent wound dressings which do not adhere to exposed tissues and which may additionally be used to deliver medicaments to the wound site.

The drug delivery devices and wound dressings of the present invention are comprised of hydrophilic polymer blends, which may, for example, comprise compositions such as those described in U.S. Pat. No. 4,300,820 (K. R. Shah) entitled "Water Absorptive Compositions", and U.S. patent application Ser. No. 606,794, filed May 3, 1984 in the name of Kishore R. Shah.

It is accepted in the medical arts that the use of water vapor-permeable, but liquid water and bacterial barrier membranes, on skin wounds is a preferred method of wound healing management.

Indeed, there are numerous patents describing such devices which have employed varying construction materials in order to achieve the desired ends, see e.g. U.S. Pat. Nos. 3,419,006, 3,557,516, 4,413,621, and published European patent application No. 81300847.1.

In general, the prior art devices made from conventional materials may include two broad compositional categories; i.e. those comprised of hydrogels and those comprised of non-hydrogel materials.

Products utilizing non-hydrogel materials offer a number of advantages. Apart from providing generally high tensile strength, water vapor permeability, liquid water and bacterial barrier properties and transparency, these non-hydrogel products are usually utilized in conjunction with a pressure-sensitive, hypoallergenic adhesive which functions primarily to secure the wound dressing in place, thus prohibiting or greatly limiting bacterial contamination when properly applied to the wound site.

However, these prior art non-hydrogel material wound dressings have a number of drawbacks. Firstly, because these non-hydrogel materials are liquid water barriers and therefore non-absorbent, the dressings may become readily detached from the wound application region when an excess of tissue fluid accumulates at the dressing-tissue interface site.

Secondly, administration of medicaments through the liquid water barrier layer film is essentially impossible. Although a number of patents teach the incorporation of drugs into either the adhesive, e.g. U.S. Pat. No. 4,310,509, or the backing, e.g. U.S. Pat. No. 4,340,043, to address this concern, such materials restrict the physicians' choice of drug therapies by offering only a limited selection of incorporated releasable compounds.

Thirdly, these conventional materials do not impart an additional degree of comfort to the patient such as found in the hydrophilic polymer blend devices of the present invention. Although perhaps less painful than traditional gauze dressings, the conventional non-hydrogel polymeric materials are not soothing to the wound area.

Recently, conventional hydrogel-type wound dressing materials have become available which correct some of the disadvantages associated with the non-hydrogel prior art wound dressings. Conventional hydrogels, having a high water content, may permit water-soluble drugs to migrate through the hydrogel film without disruption of its bacterial barrier properties. (See e.g. U.S. Pat. No. 3,419,006.)

Additionally, the conventional extremely soft water-swollen hydrogel material imparts a cooling or soothing sensation upon application to the skin, which is particularly important at inflamed and sensitive areas. However, conventional hydrogel dressings do not readily adhere to exposed wound tissue. Therefore, an additional means of anchoring the dressing to the wound area, so as to maintain an anti-bacterial seal, is required. In addition, some conventional hydrogel materials, being non-thermoplastic, are quite difficult to apply, requiring in situ formation of the barrier film. (see U.S. Pat. Nos. 3,577,516 and 4,287,177.) As a consequence, the cumbersome in situ formation of these conventional hydrogel products creates difficulties in their use.

The present invention provides a hydrophilic laminate composition which is comprised of layers of both pressure-sensitive and non-pressure-sensitive materials, at least the non-pressure-sensitive layer being capable of forming a hydrogel. Preferably, both layers are capable of forming hydrogels. These laminate structures are particularly useful for wound dressings. Such dressings are characterized by high absorbency, strength, mechanical integrity, comfort, transparency, and bacterial barrier properties. Further, these dressings may be utilized in certain drug therapies either by incorporating medicaments into the hydrophilic polymer blend materials prior to application of the dressing to the wound site or by applying the drug to the wound site by penetration through the hydrophilic polymer blends.

SUMMARY OF THE INVENTION

An object of the present invention is to provide an improved wound dressing material.

A further object of the present invention is to provide an improved transdermal, and/or topical drug, and/or bioactive agent, delivery system.

Yet another object of the present invention is to provide a wound dressing material comprised of a transparent, absorbent, hydrophilic polymer blend, which may additionally be used to deliver medicaments to the wound site.

Another object of the present invention is to provide a moisture-vapor permeable wound dressing with an adhesive layer, all layers of which are hydrophilic polymer blend compositions.

The above and other objects are accomplished by employing a multilayered laminate construction of hydrophilic polymer blend compositions which may also contain non-volatile water-soluble plasticizer at varying levels in preferred laminate constructions. The herein described laminate structures comprise, as essential layers, (1) at least one non-tacky non-pressure-sensitive layer, which is capable of forming a hydrogel upon equilibration in water and which imparts strength, and bacterial barrier properties to the structure; and (2) at least one tacky pressure-sensitive adhesive layer for attachment to skin.

It is not essential to the practice of this invention that these layers be contiguous, i.e. with the opposed surfaces laminated. It is, however, essential that they be in liquid contact so that fluid may be readily transformed from one layer to the other. Accordingly any intermediate layer(s) must be hydrophilic. In addition to these essential layers, the laminate may include other layers providing specific desired functions, the presence of which per se comprises no part of this invention.

Either the tacky, pressure-sensitive, or the non-tacky, non-pressure-sensitive layer, or both may contain releasable bioactive agents. Further, the hydrophilic material being relatively water-free at the time of skin application, is readily absorbent and easy to apply. Thus, the present invention is a unique wound dressing composite which overcomes the drawbacks of the prior art constructions.

Drugs, medicaments, or biologically active agents, if desired, may be incorporated in the laminate device, preferably in its non-tacky non-pressure-sensitive layer, although it is possible to incorporate a drug in the tacky adhesive layer, as well. Such a laminate construction when applied to the skin or wound site can deliver a drug or other agent to the skin surface. If the chosen drug has the requisite permeability through skin, the laminate may be readily utilized for transdermal drug delivery. Transport of drug occurs by a process of diffusion through the moist layers of the hydrophilic polymer blend laminate. Control of the drug release can also be accomplished by an appropriate choice of polymeric constituents in the non-tacky layer of the laminate.

For the above and other objects, the present invention describes a pressure-sensitive hydrophilic laminate composite comprising, in fluid contact, layers of a tacky pressure-sensitive adhesive hydrophilic polymer blend, and a non-tacky hydrophilic polymer blend, at least the pressure-sensitive layer further including a non-volatile plasticizer. Numerous variations in individual layer formulations allow for a multitude of hydrophilic blend laminate composite structures, which are readily utilizable as wound dressings, and/or transdermal and topical delivery systems incorporating a wide range of bioactive agents. The hydrophilic laminate composite structures are characterized by ease of application, adhesiveness to skin, mechanical integrity, transparency, fluid absorbency, and highly effective bacterial barrier properties, and permeability to water vapor, oxygen and drugs and/or bioactive agents.

As will be detailed with more particularity hereinafter, the hydrophilic polymer blends employed in the practice of this invention comprise mixtures of a water-soluble, hydrophilic polymer and a hydrophobic water-insoluble polymer, the blend or mixture being characterized as hydrophilic.

DETAILED DESCRIPTION OF THE PREFERRED EMBODIMENTS OF THE PRESENT INVENTION

The preferred laminate constructions of this invention are comprised of a nontacky, non-pressure-sensitive layer, and a tacky, pressure-sensitive adhesive layer, both of which are comprised of suitably plasticized hydrophilic polymer blends and are capable of forming a hydrogel upon equilibration in water.

These blends are further preferably comprised of either a water-soluble homopolymer of N-vinyl lactam, or a water-soluble copolymer of an N-vinyl lactam with 1 to 70 mole percent of copolymerizable monomer containing ethylenic unsaturation, and a water-insoluble copolymer. The latter water-insoluble copolymer may consist of from about 50 to 90 percent by weight, based on the total weight of the copolymer, of a hydrophobic water insoluble ethylenically unsaturated monomer, 2 to 12 percent by weight of an ethylenically unsaturated monomer containing an acid group, and 0 to 50 percent by weight of a hydrophilic ethylenically unsaturated monomer, free from acid groups.

The above blends are further characterized by a microphase separated morphology, in which the major polymeric component forms the continuous phase, and the minor polymeric component forms the dispersed phase.

Preferred embodiments of suitable water-soluble polymeric components of the hydrophilic polymer blends include poly (N-vinyl 2-pyrrolidone), and poly (N,N-dimethyl acrylamide-co-N-vinyl 2-pyrrolidone), (70:30 mole ratio), and a typical water-insoluble polymer which may be employed in the blends is a copolymer of 72 percent by weight of n-butyl methacrylate 23 percent methacrylamide, and 5 percent acrylic acid. Other examples of the water-soluble and water-insoluble components of the hydrophilic polymer blends are described in the above-referenced patent.

In the construction of the laminate structures, it may be preferred to additionally plasticize the polymer blends with a suitable nontoxic, water-soluble plasticizer, in order to impart flexibility and conformability, and in addition, pressure-sensitive adhesive characteristics to the layer, which is to be applied to skin. The suitable plasticizers which may be used, include, but are not limited to, poly(ethylene oxides)—within the molecular weight range of 200–800, glycerine, and ethylene oxide-propylene oxide copolymers. Other nontoxic, water-soluble, high boiling liquids may also be used as plasticizers.

The essential construction of the laminate structure is a tacky, pressure-sensitive adhesive component layer, hereinafter described as Layer I, and a non-tacky, non-pressure-sensitive adhesive component layer of the wound dressing composition, hereinafter referred to as Layer II.

The particular hydrophilic polymer blends of the present invention have markedly superior physical properties to the common generally used hydrogels of commerce. Hereinafter, the following definitions will apply:

Component A is a water soluble, hydrophilic polymer consisting of either a polymer of N-vinyl-2-pyrrolidone, or a copolymer of N,N-Dimethacrylamide and N-vinyl-2-pyrrolidone. The preferred level of each of the monomers in the copolymer is 70 percent N,N-Dimethacrylamide and 30 percent N-vinyl-2-pyrrolidone.

Component B is a relatively hydrophobic water-insoluble polymer comprised of n-butyl methacrylate, methacrylamide and acrylic acid. The preferred concentration range of each of the monomers in the terpolymer is about 55 to 80 percent butyl methacrylate, about 15 to 35 percent methacrylamide, and about 2 to 12 percent acrylic acid.

Component A blended with component B constitute the base hydrophilic polymer blend resin.

Component C is preferably either polyethylene glycol, having a number average molecular weight of about 200 to about 800, or glycerin. Further, it is functioning as a plasticizer, and as such may be described in parts per hundred (phr) of the base hydrogel resin.

In the most preferred embodiment of this invention, Layer I which is pressure-sensitive, and Layer II, which is non-pressure-sensitive, each comprises a mixture of the aforementioned components A,B and C and each is capable of forming a hydrogel. In accordance with the present invention, it has been found that whether a layer is pressure-sensitive or not is in part dependent upon the amount or proportions of hydrophilic polymer in the blend and is in part dependent upon plasticizer level. In general, with the aforementioned blend of polymers, for the layer to be tacky or pressure-sensitive, the formulation should contain at least 80 percent (80%) of the hydrophilic, water-soluble component A and plasticizer levels on the order of at least 50 phr.

In the practice of this preferred aspect of the invention, the useful range of components, i.e. components A, B, and C, in Layer II formulations is from about 40 percent to about 80 percent component A by weight, about 20 percent to about 60 percent component B, with from 0 to about 40 phr component C.

The useful range of components in Layer I formulations is from 80 percent to 90 percent component A by weight, 10 percent to 20 percent component B, with from 50 to 90 phr component C.

Note that when 80 percent component A is used in both Layer I and II formulations, the plasticizer level determines the pressure-sensitive behavior of the hydrogel.

Required formulations of Layers I and II may be obtained by dissolving components A, B, and C in appropriate portions, in a suitable solvent system. Suitable solvents include: propylene glycol monomethylether (PGME), mixtures of PGME and methanol, 2-methoxyethanol, dimethylformamide, and a number of other solvents. After blending together, solutions of the polymer blends may be cast into a film onto a variety of substrates and dried, or the polymer may be dried, granulated, and melt processed into the desired profile. Separate formulations of Layers I and/or II may then be joined together by lamination, by transfer coating techniques, or other similar processes.

For wound dressing applications it is considered useful to laminate Layer I and II materials together followed by lamination of a release liner (silicone-treated paper or polyethylene) to Layer I of the laminate. Such structures may then be sterilized and used as wound covering devices by removing the release liner and securing the dressing to a wound site by pressing the tacky surface of Layer I to the tissue surrounding the wound.

In practice, it has been found that the useful range of components in Layer II is from about 40 percent to about 80 percent by weight water-soluble polymers and from about 20 percent to about 60 percent of the water-insoluble polymer by weight, and from about 20 to about 40 parts by weight of the plasticizer per hundred parts (phr) by weight of the polymer blend.

The preferred concentration range of components in Layer I is from about 80 percent to about 90 percent of the water-soluble polymer by weight, from about 10 percent to about 20 percent of the water-insoluble polymer, and from about 50 to about 90 parts by weight of the plasticizer per hundred parts (phr) by weight of the polymer blend.

There are several different possible methods by which the laminate structures may be prepared, for example:

(a) Solution casting;
(b) Extrusion of film followed by pressure lamination;
(b) Coextrusion of individual blends; and
(d) Compression molding.

Method of preparing the above-mentioned formulations in a preferred embodiment will now be described in greater detail.

The hydrophilic polymer blends of Layers I or II may be obtained by dissolving the respective polymers and the plasticizer in the desired proportions in a suitable solvent system, and then removing the solvent by evaporation in vacuum at 70°-100° C.

Suitable solvents include, propylene glycol monomethyl ether (PGME), mixtures of PGME and methanol, 2-methoxyethanol, dimethylformamide, etc. The solutions may also be dried in a container, cryogenically granulated, and melt processed into the desired configuration.

Melt processing may be affected by compression molding of dried polymer blend component particles in a heated platen press. Typically, temperatures of up to about 200° C., at pressures of about 10-15 atmospheres, for periods of about 1-3 minutes, have been employed. Alternatively, dried polymer blend particles may be extruded using conventional screw extruders through slot dies into films. The individual layers may also be joined together by lamination, transfer coating, or other similar processing methods. For example, casting of a solution of a particluar polymer blend composition onto a preformed film of a second polymer blend composition in a conventional oven coating line has been employed. Further, films of two or more separate polymer blend compositions have been laminated by pressing between heated platens. A third method employed is coextrusion of the separate polymer blend compositions using a suitable coextrusion die, such as a Clorin Die. The laminate composite once formed may then be applied to a desired wound area.

The following illustrative examples will serve to describe the invention in more detail. These examples, however, are not to be construed as the limits of the invention.

EXAMPLE I

Preparation and Properties of Non-Pressure Sensitive Hydrophilic Polymer Blend Films Several mixtures of from about 40 percent to about 80 percent by weight of a copolymer of N,N-dimethylacrylamide (70%) and N-vinyl-2-pyrrolidone (30%), from about 20 percent to about 60 percent of a terpolymer comprised of N-butyl-methacrylate (78%)-methacrylamide (15%) and acrylic acid (7%), and about 25 pph of a 400 molecular weight (m.w.) polyethylene glycol (Carbowax 400 ™ —Union Carbide), were prepared by dissolving in 2-methoxyethanol. The solutions were then dried at 80°-85° C. under 20-25 inches Hg for two hours, followed by further drying at 40°-45° C. and 25-30 inches Hg for 12 hours. The dried blends were then wrapped in 0.001 inch thick Mylar and placed in dry ice for 20-30 minutes. After freezing, the samples were transferred to a stainless steel Waring blender and ground at high speed for 20-30 seconds. The resulting powders were then dried for 24 hours at 40°-45° C. and 25-30 inches Hg. The powders were then molded into 0.010 inch thick sheets using a platen press (Wabash Model 12-12-2T) at 180° C., 10 atmospheres pressures, for 3 minutes. The sheets were then hydrated in deionized water for 24 hours. The mechanical behavior of the hydrated sheets was determined by destructive testing on a universal tensile testing machine (Instron model 1122). The results are shown in Table I.

TABLE I

Properties of Polymer Blends

| PERCENT COPOLYMER IN BLEND | ULTIMATE TENSILE STRENGTH (PSI) | ULTIMATE ELONGATION (%) |
| --- | --- | --- |
| 80 | 64.4 | 337 |
| 70 | 130.8 | 298 |
| 60 | 260.2 | 274 |
| 50 | 454.4 | 258 |
| 40 | 714.7 | 244 |

The above example defines a useful range of polymer blend compositions for the non-pressure-sensitive layer of the laminate. Layer II can also be based on 100 percent (poly) vinyl-pyrrolidone or another vinyl-pyrrolidone copolymer as the Polymer A component to be blended with Polymer B. Layer I formulations are summarized in Example II.

EXAMPLE II

Preparation and Properties of Pressure sensitive Hydrophilic Polymer Blend Films Mixtures of from about 80 percent to about 90 percent of a 360,000 molecular weight (m.w.) homopolymer of N-vinyl-2-pyrrolidone (GAF Corp.—K90), and from about 10 percent to about 20 percent of the terpolymer as in Example I above, by weight, were combined with from about 50 to about 90 pph of Carbowax 400 TM by weight by dissolving in propylene glycol monomethylether (PGME), containing 5 percent methanol. Films were then prepared by casting, using a conventional Gardner casting knife, onto 0.005 inch thick Mylar sheets, and dried at 100° C. for 15 minutes. The resulting dried film samples, on a Mylar backing, were then tested for probe tack by using the "Polyken Probe Tack Tester TM" (ASTM - D2979-71), and for adhesion to steel in accordance with ASTM method D1000. The results are shown in Table II (below).

TABLE II

PROPERTIES OF PRESSURE SENSITIVE POLYMER BLEND FILMS

| PVP In Blend (%) | Carbowax 400 TM (phr) In Blend | Probe Tack (g/cm²) | Adhesion to Steel (oz/in) |
| --- | --- | --- | --- |
| 80 | 50 | 0 | 0 |
| 80 | 60 | 0 | 0 |
| 80 | 70 | 45 | 3.5 |
| 80 | 80 | 75 | 5.7 |
| 90 | 50 | 34 | 1.5 |
| 90 | 60 | 114 | 5.5 |
| 90 | 70 | 168 | 7.7 |
| 90 | 80 | 247 | 12.4 |

Probe tack valves of over 100 indicate good pressure sensitive properties. Adhesion to steel valves are shown to indicate reasonable performance but are not necessarily applicable to predict adhesion to skin.

EXAMPLE III

Effect of Polymer Blend Compositions of Film Hydration Levels

The hydration level of various hydrogels was determined by mixing poly (vinyl pyrrolidone) and the terpolymer of Example I in a suitable solvent and isolating the resultant blend by evaporation of the solvent under vacuum at 100° C. From the obtained dry powders, approximately 8-12 mil thick sheets of blends were prepared by compression molding as described in Example I. The water content of the hydrogels was determined by the difference in weights of the blend samples before and after 24 hour immersion in water. Surface water on the hydrated samples was removed prior to weighing by blotting between filter paper. Table III (below) summarizes the data.

TABLE III

EQUILIBRIUM WATER CONTENT OF HYDROPHILIC BLEND FILMS

| PVP in Blend (%) | Water in Film (%) |
| --- | --- |
| 90 | 84 |
| 80 | 77 |
| 70 | 64 |
| 60 | 55 |

EXAMPLE IV

Effect of Polymer Blend Composition on Drug Release Rate

Various hydrogel polymer blends were prepared by dissolving from about 30 percent to about 70 percent poly (vinyl pyrrolidone) (GAF K90) by weight, from about 30 percent to about 70 percent of the terpolymer as in Example I, with about 10 percent by weight, of the total polymer blend weight, of hydrocortisone in 2-methoxyethanol. The polymer blend solutions containing the hydrocortisone were then dried and powdered as shown in Example I.

The resultant powders were then compression molded above (i.e. Wabash Press) into disks measuring 0.75 inch in diameter and 0.026 inch in thickness. The rate of diffusion of hydrocortisone out of the disk was monitored by placing the disks in deionized water at 25° C., under constant agitation, with samples being periodically removed. The time to diffuse 50 percent of the initial hydrocortisone from the disks is summarized in Table IV (below).

TABLE IV

EFFECT OF POLYMER BLEND COMPOSITION ON HYDROCORTISONE RELEASE

| PVP in Blend (%) | Time to 50% Drug Released (Days) |
| --- | --- |
| 70 | 1 |
| 50 | 3 |
| 30 | 8 |

EXAMPLE V

Preparation of a Typical Laminate

A non-pressure sensitive hydrogel blend film was prepared as in Example I having 40 percent by weight of the terpolymer in the blend. A pressure sensitive hydrogel blend film was prepared as in Example II having 80 percent of poly (N-vinyl-2-pyrrolidone), along with 80 pph of Carbowax400 TM.

The resultant cast films were then placed in contiguous apposition with the Mylar sheets outermost. This sandwich was then placed on a firm glass surface, and compressed by rolling with a rubber-coated, weighted (5 pounds) wheel.

Subsequently, both Mylar support sheets were removed from the composite. Upon application of the resulting composite to human skin, via the pressure sensitive surface, significant adhesion and conformability was noted.

We claim:

1. A hydrophilic polymer blend laminate for use as a wound dressing and/or as a drug delivery construction, comprising:

at one non-pressure-sensitive adhesive hydrophilic polymer blend layer adapted for forming a hydrogel upon equilibration with water, said layer being characterized by imparting strength and bacterial barrier properties to said laminate composite;

and at least one pressure-sensitive adhesive hydrophilic polymer blend layer adapted for attachment to skin, said layers being in fluid contact.

2. A laminate composite as defined in claim 1 wherein said layers are contiguous.

3. A laminate composite as defined in claim 1 wherein at least one of said layers further includes a bioactive agent.

4. A laminate composite as defined in claim 3 wherein said bioactive agent is a topical medicament incorporated in said non-pressure-sensitive adhesive layer.

5. A laminate composite as defined in claim 2 wherein both said layers are adapted for forming an hydrogel.

6. A hydrophilic polymer blend laminate composite, as defined in claim 2, wherein said layers are further comprised of various percents of blends of:

(1) a water-soluble polymer selected from the group consisting of a homopolymer of an N-vinyl lactam, and a copolymer of N-vinyl lactam, with from 1 to 90 percent of copolymerizable monomer, containing ethylenic unsaturation; and (2) a water-insoluble copolymer further comprising from about 55 to about 80 percent by weight of n-butyl methacrylate, and from 15 to about 35 percent by weight of methacrylamide, and from about 2 to about 12 percent of acrylic acid; and (3) water-soluble non-volatile plasticizer.

7. A hydrophilic polymer blend laminate composite as defined in claim 1, wherein said non-pressure-sensitive layer further comprises from about 40 percent to about 80 percent by weight of said water-soluble polymer, from about 20 percent to about 60 percent by weight of said water-insoluble polymer, and from about 15 percent to about 30 percent by weight of said water-soluble non-volatile plasticizer.

8. A hydrophilic polymer blend laminate composite as defined in claim 1, wherein said pressure-sensitive layer further comprises from about 80 percent to about 90 percent by weight of said water-soluble polymer, from about 10 percent to about 20 percent of said water-insoluble polymer, and from about 33 percent to about 47 percent by weight of said water-soluble non-volatile plasticizer.

9. A hydrophilic polymer blend laminate composite as defined in claim 1, wherein said water-soluble non-volatile plasticizer is selected from the group consisting of:

polyethylene glycol, having a molecular weight of from about 200 to about 800, ethylene oxide-propylene oxide copolymers, and glycerine.

10. A hydrophilic polymer blend laminate composite as defined in claim 1, wherein said water-soluble polymer comprises a homopolymer of N-vinyl-2-pyrrolidone, and copolymers of N-vinyl-2-pyrrolidone and N,N-Dimethylacrylamide.

* * * * *